(12) United States Patent
Ra Speret

(10) Patent No.: US 11,065,416 B2
(45) Date of Patent: Jul. 20, 2021

(54) THERAPEUTIC DEVICE

(71) Applicant: Bena Ptah Tehuti Ra Speret, Greensboro, NC (US)

(72) Inventor: Bena Ptah Tehuti Ra Speret, Greensboro, NC (US)

( * ) Notice: Subject to any disclaimer, the term of this patent is extended or adjusted under 35 U.S.C. 154(b) by 265 days.

(21) Appl. No.: 16/245,239

(22) Filed: Jan. 10, 2019

(65) Prior Publication Data
US 2019/0209805 A1     Jul. 11, 2019

Related U.S. Application Data

(60) Provisional application No. 62/615,528, filed on Jan. 10, 2018.

(51) Int. Cl.
| | | |
|---|---|---|
| *A61M 21/02* | (2006.01) | |
| *A61M 11/04* | (2006.01) | |
| *A61L 9/12* | (2006.01) | |
| *G10H 1/00* | (2006.01) | |
| *A61L 9/14* | (2006.01) | |
| *A61M 21/00* | (2006.01) | |

(52) U.S. Cl.
CPC ............ *A61M 21/02* (2013.01); *A61L 9/12* (2013.01); *A61L 9/122* (2013.01); *A61M 11/042* (2014.02);
(Continued)

(58) Field of Classification Search
CPC .... A61M 2205/505; A61M 2021/0022; A61M 2205/3584; A61M 2021/0038;
(Continued)

(56) References Cited

U.S. PATENT DOCUMENTS 4,781,895 A * 11/1988 Spector ............... A01M 1/2088
261/DIG. 88
5,353,546 A * 10/1994 Bock ...................... A47G 7/06
239/51.5
(Continued)

FOREIGN PATENT DOCUMENTS

WO      WO-0164257 A1 *  9/2001  ............... A61L 9/03

OTHER PUBLICATIONS

IMounTEK Pyramid Shape 7 LED 6 Sounds/120 ML Ultrasonic Aromatherapy Essential Oil Air Diffuser/Aroma Humidifier, iMounTEK, Dec. 1, 2017 (Year: 2017).*
(Continued)

*Primary Examiner* — Navin Natnithithadha
*Assistant Examiner* — Sunita Reddy

(57) ABSTRACT

A therapeutic device that can diffuse essential oils, infuse frequency into liquids, emit frequency-driven lights, and produce solfeggio tones. The therapeutic device includes an enclosure, at least one oil-diffusing device, at least one frequency-infusing device, at least one frequency-tone generator, a first plurality of ambience lights, at least one vent, and a first controller. The enclosure is used to conceal and protect the electronic components. The at least one oil-diffusing device is used to diffuse fluids. The at least one frequency-infusing device is used to infuse frequency by vibration into fluids. The at least one frequency-tone generator is used to generate tones of different frequencies. The first plurality of ambience lights is used for aesthetic and therapeutic aspects. The at least one vent is used as an escape for the mist produced by the diffusion of the fluids. The first controller is used to manage the electronic components.

10 Claims, 5 Drawing Sheets

(52) U.S. Cl.
CPC ............... *G10H 1/00* (2013.01); *A61L 9/14* (2013.01); *A61L 2209/11* (2013.01); *A61L 2209/12* (2013.01); *A61L 2209/132* (2013.01); *A61L 2209/135* (2013.01); *A61M 2021/0038* (2013.01)

(58) Field of Classification Search
CPC ...... A61M 2205/3592; A61M 2205/42; A61M 2202/04; A61M 2205/3561; A61M 11/042; A61M 2206/10; A61M 21/02; A61M 11/005; A61M 2021/0016; A61M 2021/0027; A61M 2205/07; A61M 2021/0044; G10H 1/00; G10H 1/26; A61L 2209/11; A61L 9/14; A61L 2209/135; A61L 2209/12; A61L 2209/132; A61L 9/12; A61L 9/122
USPC ........................................................ 600/26–28
See application file for complete search history.

(56) References Cited

U.S. PATENT DOCUMENTS

| | | | | |
|---|---|---|---|---|
| 5,827,483 | A * | 10/1998 | Fullam | A61L 9/03 422/122 |
| 6,290,713 | B1 * | 9/2001 | Russell | A61N 5/0616 607/88 |
| 6,478,440 | B1 * | 11/2002 | Jaworski | A01M 1/04 362/253 |
| 2001/0053283 | A1 * | 12/2001 | Levine | A61L 9/02 392/395 |
| 2009/0073694 | A1 * | 3/2009 | Scannell, Jr. | A47G 7/06 362/253 |
| 2011/0268605 | A1 * | 11/2011 | Haran | B05B 17/0646 422/4 |
| 2014/0067130 | A1 * | 3/2014 | Pillai | A61M 21/02 700/275 |
| 2014/0158129 | A1 * | 6/2014 | Pratt, Jr. | A61M 11/042 128/203.26 |
| 2014/0319238 | A1 * | 10/2014 | Su | A45D 34/00 239/70 |
| 2018/0099068 | A1 * | 4/2018 | Pitcher | F04B 13/02 |
| 2018/0099105 | A1 * | 4/2018 | Pitcher | F04F 1/18 |
| 2019/0083719 | A1 * | 3/2019 | Freeman | B01F 3/0407 |
| 2019/0118210 | A1 * | 4/2019 | Freeman | B05B 17/0615 |
| 2019/0209806 | A1 * | 7/2019 | Allen | G05B 15/02 |

OTHER PUBLICATIONS

"This levitating incense holder will help you get through 2017", Phillip Tracy, dailydot, May 31, 2017 (Year: 2017).*

* cited by examiner

THERAPEUTIC DEVICE

The current application claims a priority to the U.S. Provisional Patent application Ser. No. 62/615,528 filed on Jan. 10, 2018.

FIELD OF THE INVENTION

The present invention relates generally to tone generators and essential oils diffusers. More specifically, the present invention is a therapeutic device that can generate essential oil aromatherapies, infuse frequency into fluids, and generate combinations of frequency tones.

BACKGROUND OF THE INVENTION

Aroma/Sound/Vibration/Color healing is nothing new. They have been successfully implemented in numerous forms all over the world for thousands of years. Aromatherapy generally uses plant materials and various aromatic plants oils as well as other aroma compounds for improving psychological or physical well-being and healing. At an aromatherapy session, a patient may be directed to breathe in essential oils directly from a scented device, such as a piece of cloth, or indirectly through steam inhalations, vaporizers, or sprays. Oftentimes, essential oils are steamed, vaporized, etc., using a device, usually a diffuser.

A diffuser is generally a device which receives an amount of water-diluted essential oils and vaporizes the essential oils and consequently generates ultrasonic frequencies which diffuse the vaporized essential oils around an area. Ultrasonic diffusion is preferable to the other classical forms of diffusion (nebulization, evaporation, etc.) due to the fact that the quality of the essential oils does not degrade.

While aromatherapy is efficient as an alternative for infection, stress, and other health problems, there are no existing methods or devices which combine the aromatherapy benefits with the benefits of Solfeggio tones. The Solfeggio tones incorporate the vibration aspect of therapy into the device. Solfeggio frequencies make up the seven-tone scale traditionally used in music and correspond to the seven chakra energy centers in the body. Each Solfeggio tone comprises a frequency which can balance a person's energy and keep a person's body, mind and spirit in perfect harmony. While the healing properties of Solfeggio tones are known, there are no systems or devices which combine aromatherapy with Solfeggio tones to amplify the benefits from each.

Furthermore, the present invention is able to infuse frequencies into fluids such as, but not limited to, water and/or essential oils. The produced frequency-infused water can be consumed by the user in order to remove toxins and/or prevent toxins from entering the user's body. Additionally, the user can infuse frequencies into fluids and then diffuse the frequency-infused fluid in order to generate a high-quality aromatherapy experience.

The audible Solfeggio tones generated by the present invention also correspond to sound therapy, which addresses health issues via the auditory relationship of sound to healing, while color therapy is the visual therapeutic contributor of the device. The present invention brings structured self-therapy to the consumer. Thus, a device which combines the benefits of aroma, sound, vibration, and color therapy into the convenience of one spiripeutic locus for all the senses is beneficial and necessary.

The primary objective of the present invention is to provide a therapeutic device which combines the benefits of aroma, sound, vibration, and color therapy. Another objective of the present invention is to provide a therapeutic device which infuses diluted essential oils with frequencies by vibration. Another objective of the present invention is to provide a therapeutic device which diffuses the infused diluted essential oils to the surroundings. Another objective of the present invention is to provide a therapeutic device which generates audible Solfeggio tones. Another objective of the present invention is to provide a therapeutic device which infuses water with frequency for consumption. Another objective of the present invention is to provide a therapeutic device which generates user-selected or frequency-controlled color patterns. Additional advantages of the invention will be set forth in part in the description which follows, and in part will be obvious from the description, or may be learned by practice of the invention. Additional advantages of the present invention may be realized and attained by means of the instrumentalities and combinations particularly pointed out in the detailed description of the invention section. Further benefits and advantages of the embodiments of the present invention will become apparent from consideration of the following detailed description given with reference to the accompanying drawings, which specify and show preferred embodiments of the present invention.

DETAIL DESCRIPTIONS OF THE INVENTION

Figure 1:
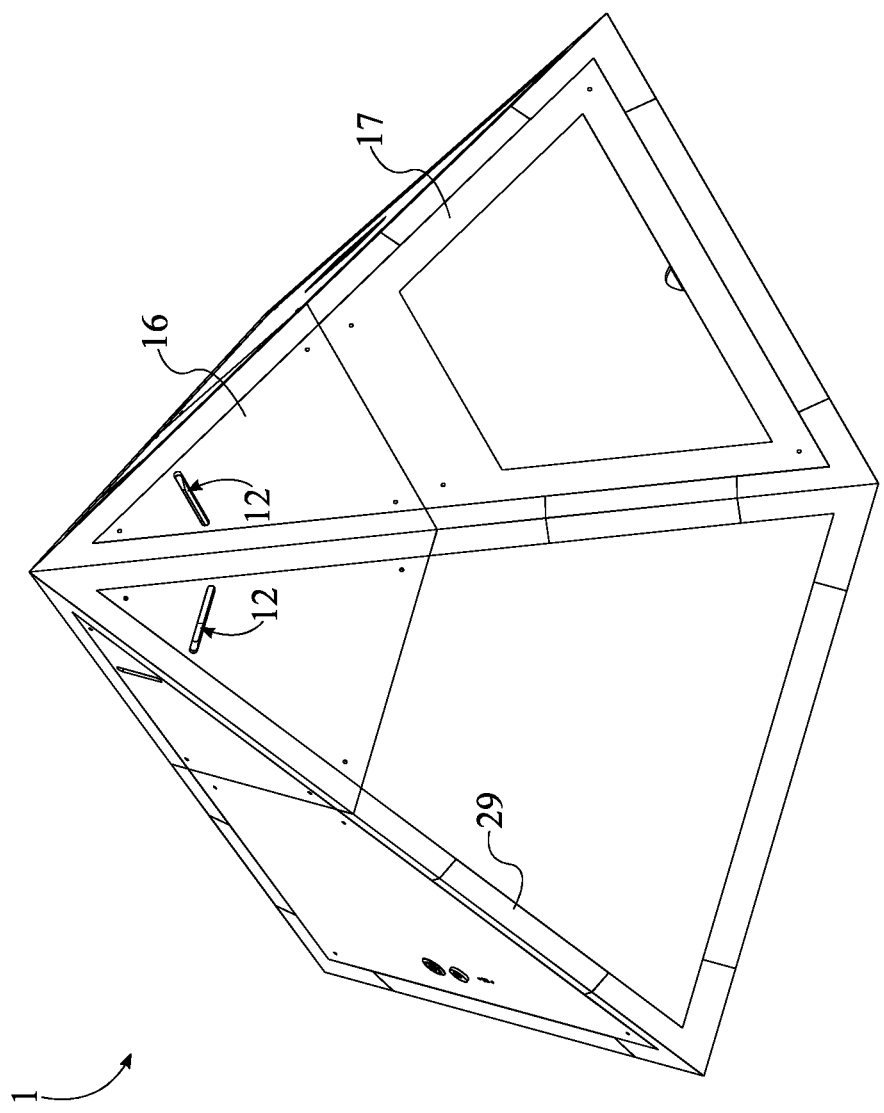
FIG. 1 is a perspective view of the present invention.

All illustrations of the drawings are for the purpose of describing selected versions of the present invention and are not intended to limit the scope of the present invention.

In reference to FIGS. 1 through 5, the present invention is a therapeutic device that can diffuse essential oils, infuse frequency into liquids, emit frequency-driven lights, and produce solfeggio tones. The present invention comprises an enclosure 1, at least one oil-diffusing device 2, at least one frequency-infusing device 8, at least one frequency-tone generator 10, a first plurality of ambience lights 11, at least one vent 12, and a first controller 13. The enclosure 1 is used to conceal and protect the electronic components of the present invention. The at least one oil-diffusing device 2 is used to diffuse fluids such as, but not limited to, water and/or essentials oils. The at least one oil-diffusing device 2 may be any type of diffuser but is preferably an ultrasonic diffuser. The at least one frequency-infusing device 8 is used to infuse frequency by vibration into fluids such as, but not limited to, water and/or essential oils. The frequency-infused fluids may be consumed by the user in order to remove toxins and/or prevent toxins from entering the user's body. The at least one frequency-tone generator 10 is used to generate tones of different frequencies such as, but not limited to, solfeggio tones. The first plurality of ambience lights 11 is used for an aesthetic aspect for the user when fluids are being diffused by the at least one oil-diffusing device 2. The first plurality of ambience lights 11 may be driven by the at least one frequency-tone generator 10. Additionally, the first plurality of ambience lights may be driven by the at least one frequency-infusing device 8. The at least one vent 12 is used as an escape for the mist produced by the diffusion of the fluids by the at least one oil-diffusing device 2. The first controller 13 is used to manage the electronic components of the present invention.

Figure 4:
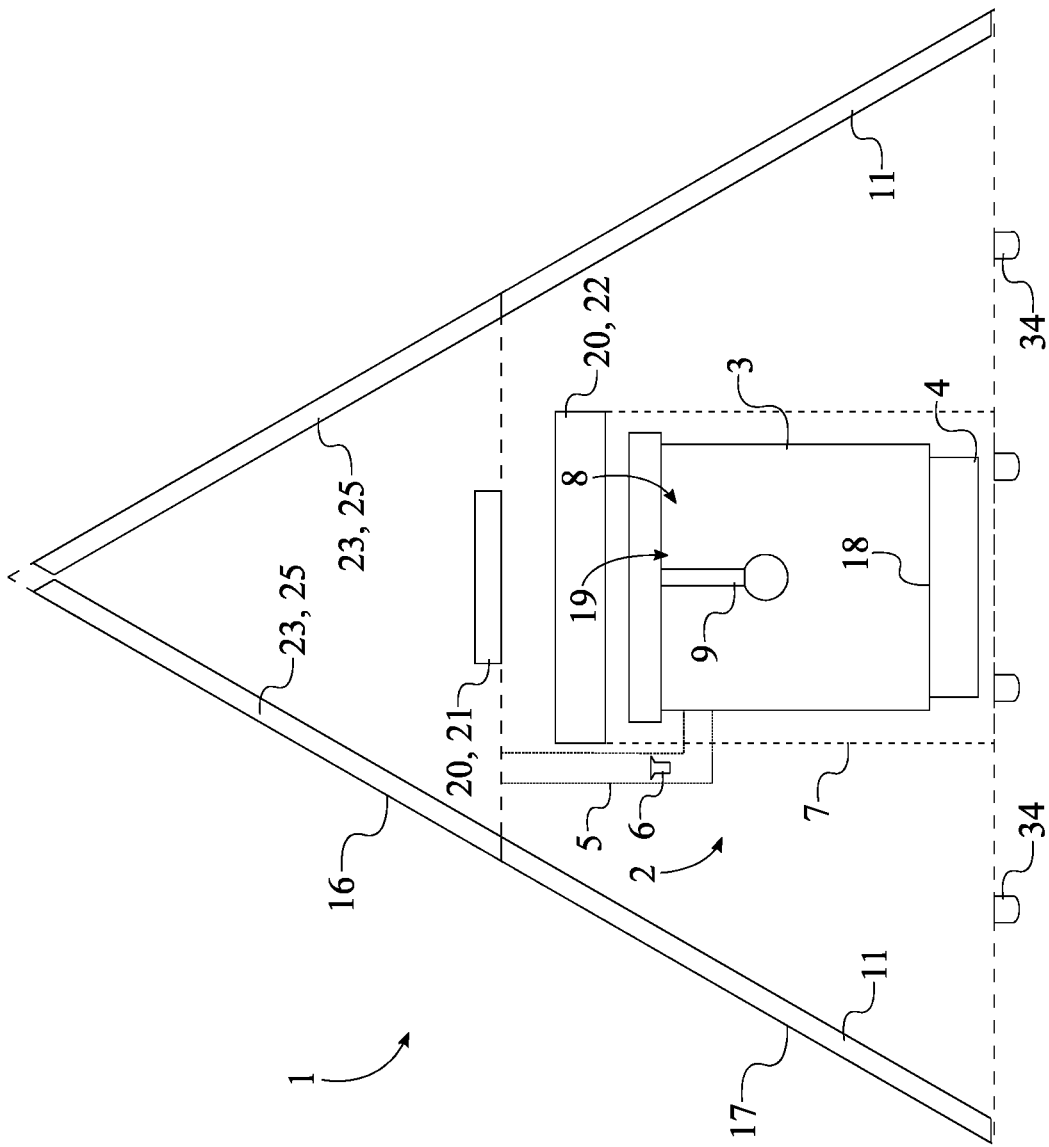
FIG. 4 is a schematic diagram displaying the internal components of the present invention.
Figure 5:
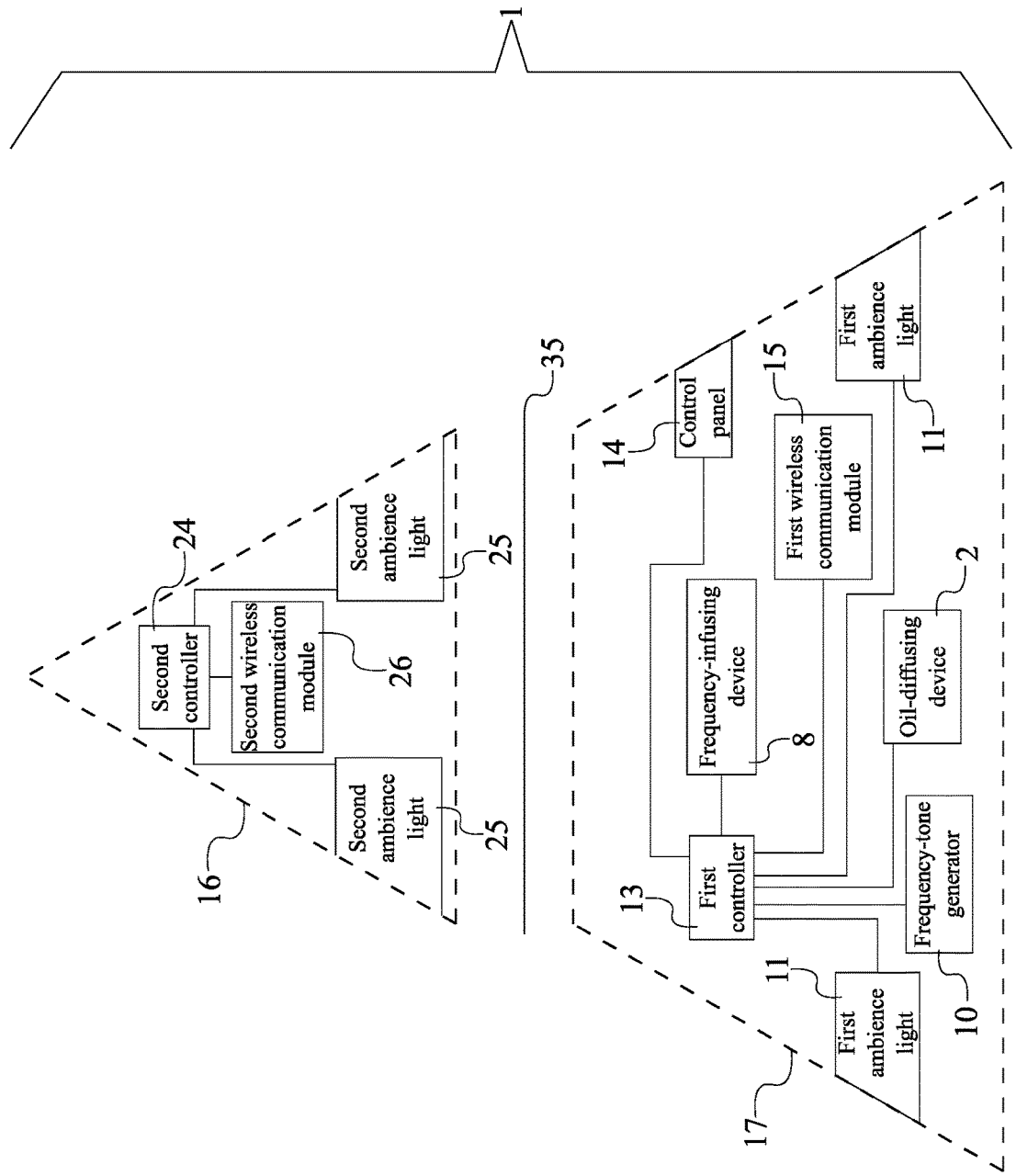
FIG. 5 is an exploded schematic diagram displaying the electronic connections of the present invention.

The general configuration of the aforementioned components allows the present invention to effectively and efficiently diffuse essential oils, induce frequency into liquids, emit frequency-driven lights, and produce solfeggio tones. With reference to FIGS. 4 and 5, the at least one frequency-tone generator 10, the at least one oil-diffusing device 2, the at least one frequency-infusing device 8, and the first controller 13 are mounted within the enclosure 1 in order to be concealed and protected from environmental risks. With reference to FIGS. 1 and 4, the first plurality of ambience lights 11 and the at least one vent 12 are integrated into the enclosure 1. This arrangement allows the first plurality of ambience lights 11 to be protected from environmental risks. Additionally, this arrangement allows the at least one vent 12 to properly act as an escape for the mist produced by the diffusion of the fluids by the at least one oil-diffusing device 2. In the preferred embodiment of the present invention, the at least one vent 12 traverses into each side of the enclosure 1. The at least one frequency-infusing device 8 is in fluid communication with the at least one oil-diffusing device 2. This arrangement allows the mist, produced from the diffusion of the fluids, to flow from the at least one oil-diffusing device 2 and out of the at least one vent 12. With reference to FIG. 5, the at least one frequency-tone generator 10, the at least one oil-diffusing device 2, the at least frequency-infusing device 8, and the first plurality of ambience lights 11 are electronically connected to the first controller 13. This allows the first controller 13 to process and communicate instructions between the at least one frequency-tone generator 10, the at least one oil-diffusing device 2, the at least frequency-infusing device, and the first plurality of ambience lights 11.

Figure 2:
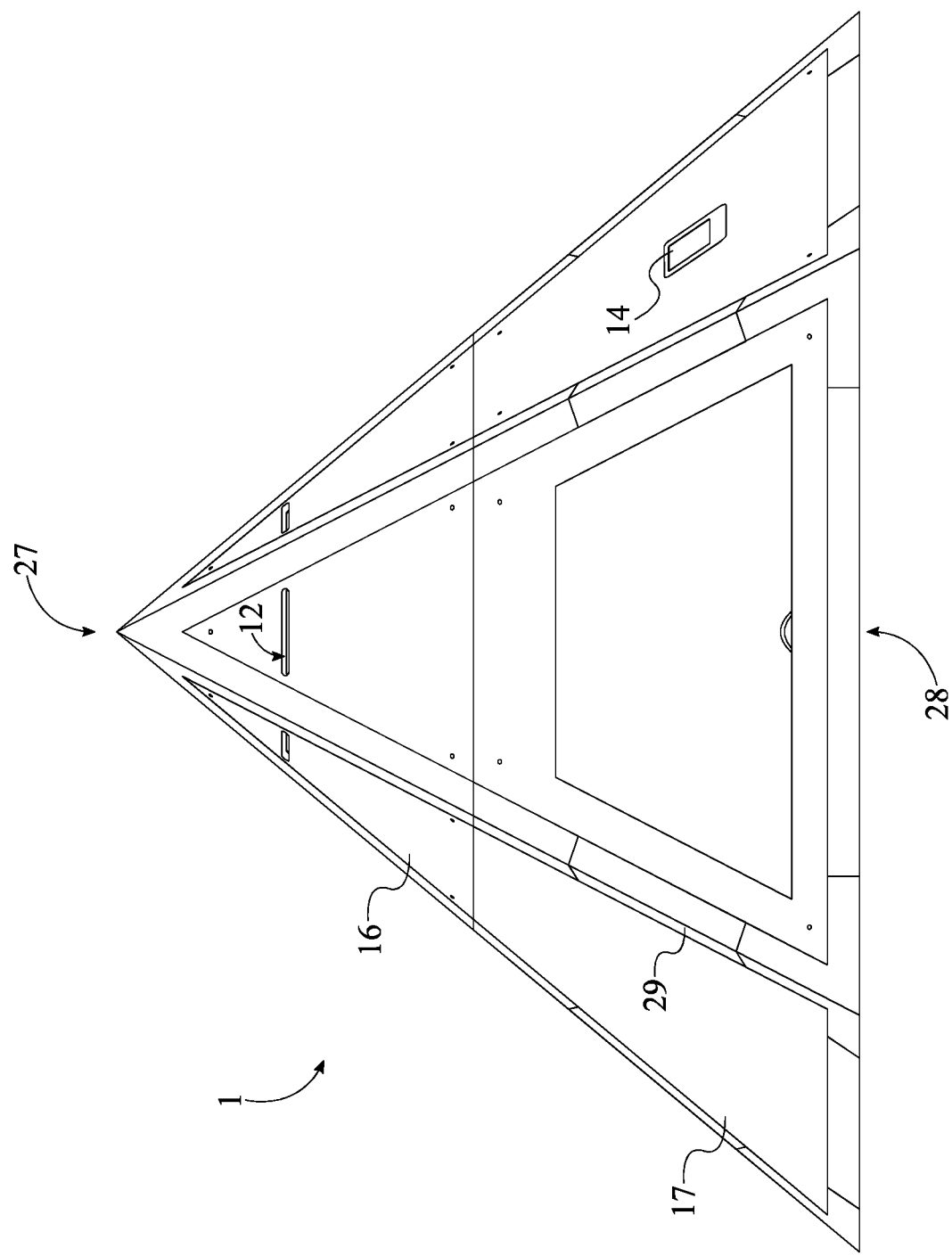
FIG. 2 is a front view of the present invention.

With reference to FIGS. 2 and 5, the present invention may further comprise a control panel 14 in order for the present invention to receive user inputs. The control panel 14 may be any type of control unit but preferably is a touch screen display. The control panel 14 is integrated into the enclosure 1 and electronically connected to the first controller 13. This arrangement allows the electronic connection between the control panel 14 and the first controller 13 to be concealed and the first controller 13 to process and read the user inputs through the control panel 14.

With reference to FIG. 5, the present invention may further comprise at least one first wireless communication module 15 in order for the present invention to wirelessly receive user inputs. The at least one first wireless communication module 15 may be a Bluetooth wireless module, a Wi-Fi wireless module, or include both a Bluetooth wireless module and a Wi-Fi wireless module. The at least one first wireless communication module 15 is mounted within the enclosure 1 and is electronically connected to the first controller 13. This arrangement conceals and protects the at least one wireless communication module and allows the first controller 13 to process and read user inputs through the at least one first wireless communication module 15.

Additionally, the present invention comprises a plurality of speakers to amplify the tones produced by the at least one frequency-tone generator 10. The plurality of speakers is integrated into the base of the enclosure and is electronically connected to the first controller 13. Furthermore, the user can play music or other similar media files through the plurality of speakers via the at least one first wireless communication module 15. This is done by wirelessly connecting the present invention to any media storage device such as, but not limited to, a mobile device or a personal computing device using the at least one first wireless communication module 15.

Figure 3:
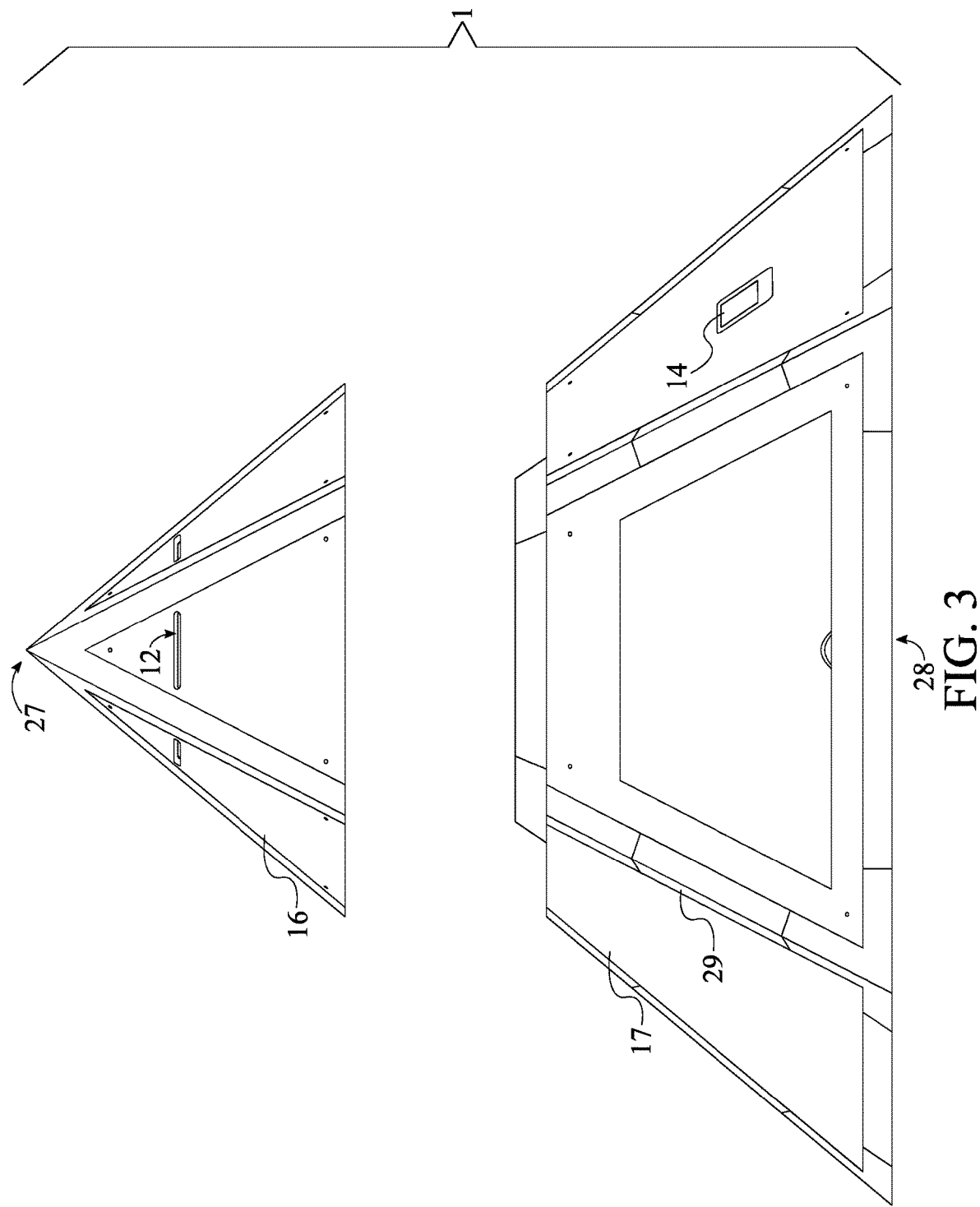
FIG. 3 is an exploded front view of the present invention.

With reference to FIGS. 2 and 3, the enclosure 1 comprises a top separable portion 16 and a bottom separable portion 17 in order to access and maintain the interior components of the present invention. With reference to FIG. 4, the at least one oil-diffusing device 2 comprises at least one reservoir 3. The at least one reservoir 3 is used to hold fluids such as, but not limited to, water and/or essential oils. The top separable portion 16 is attached onto the bottom separable portion 17 in order for a user to easily remove the top separable portion 16 when desired. In the preferred embodiment of the present invention, the top separable portion 16 is attached onto the bottom separable portion 17 by snapping onto a lid of the bottom separable portion 17. The at least one reservoir 3 is removably situated within the bottom separable portion 17 in order for the user to access and fill the reservoir with fluids. The enclosure 1 may further comprise an access-door in order to access the at least one reservoir 3. The access-door is integrated into a face of the bottom separable portion 17. Furthermore, the access-door may be slidably mounted or hingedly mounted to the enclosure 1 in order to conceal or reveal the at least one reservoir 3.

With reference to FIG. 4, the at least one oil-diffusing device 2 further comprises an ultrasonic vibrator 4, at least one exhaust 5, a blower 6, and a muffler 7. The ultrasonic vibrator 4 is the main component which is used to diffuse fluids which are poured into the at least one reservoir 3. The at least one exhaust 5 is used to release the mist produced from the diffusion of the fluids poured into the at least one reservoir 3. The blower 6 is used to drive the flow of the mist through the at least one exhaust 5. The muffler 7 is used to suppress the sound produced by the ultrasonic vibrator 4 when diffusing the fluids poured into the at least one reservoir 3. The ultrasonic vibrator 4 is mounted adjacent to a base 18 of the at least one reservoir 3 in order to properly diffuse fluids which are poured into the at least one reservoir 3. The at least one reservoir 3 and the ultrasonic vibrator 4 are enclosed by the muffler 7 in order for the muffler 7 to properly suppress the sound produced when the ultrasonic vibrator 4 is used to diffuse fluids from the at least one reservoir 3. The at least one exhaust 5 is in fluid communication with the at least one reservoir 3 in order for the mist to freely flow from the at least one reservoir 3 and through the at least one exhaust 5. The blower 6 is operatively integrated into the at least one exhaust 5, wherein the blower 6 is used to draw fluid out of the at least one reservoir 3 and to push fluid out of the at least one exhaust 5.

With reference to FIG. 4, the at least one frequency-infusing device 8 comprises a vibrating rod 9. The vibrating rod 9 is used to infuse frequency by vibration into the fluids poured into at least one reservoir 3. The vibrating rod 9 is mounted through an opening 19 of the at least one reservoir 3. This arrangement allows the vibrating rod 9 to contact the fluids poured into the at least one reservoir 3.

With reference to FIG. 4, the present invention may further comprise a magnetic levitation mechanism 20. The magnetic levitation mechanism 20 adds an aesthetic aspect when using the present invention. In further detail, the magnetic levitation mechanism 20 is used to levitate the top separable portion 16 over the bottom separable portion 17. The magnetic levitation mechanism 20 comprises a magnet 21 and a current-inducing module 22. The current-inducing module 22 is used to conduct electricity with no resistance such as, but not limited to, a superconductor. The current-inducing module 22 is mounted within the bottom separable portion 17 and is electronically connected to the first controller 13. This arrangement conceals the current-inducing module 22 and allows the first controller 13 to manage the current-inducing module 22. The magnet 21 is mounted within the top separable portion 16 and positioned adjacent to the current-inducing module 22. This arrangement conceals the magnet 21 and properly positions the magnet 21 in order to be levitated by the current-inducing module 22. Furthermore, the magnet 21 and the current-inducing module 22 are magnetically coupled to each other, which allows the top separable portion 16 to be lifted off the bottom separable portion 17 as the magnet 21 is levitated from the current-inducing module 22.

With reference to FIG. 4, the present invention may further comprise a plurality of reflectors 23. The plurality of reflectors 23 is used to reflect light emitted by the first plurality of ambience lights 11 in order to simulate the appearance that the top separable portion 16 is emitting light. The top separable portion 16 and the bottom separable portion 17 are made of a translucent material in order to allow light to pass through the enclosure 1. The first plurality of ambience lights 11 is integrated into the bottom separable portion 17 in order to protect the first plurality of ambience lights 11 while still allowing light emitted by the first plurality of ambience lights 11 to pass through the bottom separable portion 17 due to the translucent properties of the bottom separable portion 17. The plurality of reflectors 23 is integrated into the top separable portion 16 in order to conceal the plurality of reflectors 23. Furthermore, the first plurality of ambience lights 11 is in optical communication with the plurality of reflectors 23 in order for the plurality of reflectors 23 to properly reflect light emitted by the first plurality of ambience lights 11.

In another embodiment of the present invention and with reference to FIG. 5, the present invention may further comprise a second controller 24, a second plurality of ambience lights 25, and at least one second wireless communication module 26 in order for the top separable portion 16 to emit light similarly to the bottom separable portion 17. Similar to the first plurality of ambience lights 11, the second plurality of ambience lights 25 is used for an aesthetic aspect when using the present invention. The second controller 24 is used to manage the electronic components of the top separable portion 16. The at least one second wireless communication module 26 allows the second controller 24 to communicate with the first controller 13 via the at least one first wireless communication module 15. The second plurality of ambience lights 25 is integrated into the top separable portion 16 in order to conceal and protect the second plurality of ambience lights 25. The second controller 24 and the at least one second wireless communication module 26 are mounted within the top separable portion 16 in order to conceal and protect the second controller 24 and the at least one second wireless communication module 26. The second plurality of ambience lights 25 and the at least one second wireless communication module 26 are electronically connected to the second controller 24 in order for the second controller 24 to process and communicate instructions between the second plurality of ambience lights 25 and the at least one second wireless communication module 26. Furthermore, the second controller 24 is communicably coupled to the first controller 13. This arrangement allows the second plurality of ambience lights 25 to be wirelessly synchronized with the first plurality of ambience lights 11.

With reference to FIG. 1, the enclosure 1 is shaped as a pentagonal pyramid for an aesthetic aspect to the present invention. In order for the mist, produced by the diffusion of fluids by the at least one oil-diffusing device 2, to efficiently flow from out of the enclosure 1, the at least one vent 12 is positioned adjacent to an apex 27 of the pentagonal pyramid.

The present invention may further comprise a plurality of optical strips. The plurality of optical strips is used to enclose either a light from the first plurality of ambience lights 11 or a reflector from the plurality of reflectors 23. In further detail, each of the plurality of optical strips comprises an arbitrary first light from the first plurality of ambience lights 11 and an arbitrary reflector from the plurality of reflectors 23. This means that an optical strip from the plurality of optical strips is one unit that includes a reflector and a light. Each of the plurality of optical strips is positioned along a corresponding lateral edge 29 of the pentagonal pyramid. This arrangement properly positions the plurality of optical strips for an aesthetic aspect when using the present invention. The arbitrary reflector is positioned in between the arbitrary first light and the apex 27 of the pentagonal pyramid. This arrangement positions the plurality of optical strips enclosing the arbitrary reflector in the top separable portion 16 rather than the bottom separable portion 17.

In another embodiment of the present invention, each of the plurality of optical strips comprises an arbitrary first light from the first plurality of ambience lights 11 and an arbitrary second light from the second plurality of ambience lights 25. This means that an optical strip from the plurality of optical strips is one unit that includes two lights. The arbitrary second light is positioned in between the arbitrary first light and an apex 27 of the pentagonal pyramid. This arrangement positions the plurality of optical strips enclosing the arbitrary second light in the top separable portion 16 rather than the bottom separable portion 17.

With reference to FIG. 4, the present invention may further comprise a plurality of leg stubs 34. The plurality of leg stubs 34 is used to protect the enclosure 1 and the surface that the present invention is placed upon. Additionally, the plurality of leg stubs 34 is used to prevent the present invention from sliding along a surface. The plurality of leg stubs 34 is externally mounted to a base 28 of the pentagonal pyramid and distributed across the base 28 of the pentagonal pyramid. This arrangement properly positions the plurality of leg stubs 34 to the enclosure 1.

With reference to FIG. 5, a division plane 35 between the top separable portion 16 and the bottom separable portion 17 is positioned in between an apex 27 of the pentagonal pyramid and a base 28 of the pentagonal pyramid. The division plane 35 is where the top separable portion 16 attaches onto the bottom separable portion 17. Furthermore, the division plane 35 is where the separation and levitation occurs by the magnetic levitation mechanism 20. The division plane 35 between the top separable portion 16 and the bottom separable portion 17 is positioned parallel to the base 28 of the pentagonal pyramid.

The present invention can be used for various purposes. For example, the present invention can be used to diffuse plain water through the at least one oil-diffusing device 2, to diffuse essential oil-based water through at least one oil-diffusing device 2, infuse water with frequency through the at least one frequency-infusing device 8, infuse then diffuse plain water by using the at least one frequency-infusing device 8 and then the at least one oil-diffusing device 2, and to infuse then diffuse essential oil-based water by using the at least one frequency-infusing device 8 and then the at least one oil-diffusing device 2.

The present invention may further include a software application. The software application can be installed on various electronic devices which may or may not be wireless-connected to the Internet. The various electronic devices may include, but are not limited to, smartphones, tablets, laptops, desktop computers, etc. The software application may further be a cloud application and/or website which can be accessed through another application such as a browser or search engine. After the present invention is powered up, the user can adjust/modify a plurality of preferences on the menu provided on the control panel 14 or through an electronic via the at least one first wireless communication module 15. The user can adjust the color of the plurality of lights as well as other variables including, but not limited to, pattern, intensity, etc. The user can also pair the present invention to an external device as well as connect the present invention to the Internet wirelessly via the at least one first wireless communication module 15. The user can further turn on and/or select the Solfeggio tones which are to be produced by the at least one frequency-tone generator 10. The user can further turn on/off the at least one oil-diffusing device 2 and configure the at least one oil-diffusing device 2 to work at different configurations. The user can select the intensity of the at least one oil-diffusing device 2, the frequency at which the plurality of essential oils is to be infused, and the timer. In the preferred embodiment of the present invention, the present invention can be either manually or remotely operated through the application. In alternate embodiments of the present invention, the present invention may further allow the user to configure the at least one frequency-tone generator 10 and the at least one oil-diffusing device 2 to operate in different settings from the ones disclosed above.

Although the invention has been explained in relation to its preferred embodiment, it is to be understood that many other possible modifications and variations can be made without departing from the spirit and scope of the invention as hereinafter claimed.

What is claimed is:

1. A therapeutic device comprises:
an enclosure;
at least one oil-diffusing device;
at least one frequency-infusing device;
at least one frequency-tone generator;
a first plurality of ambience lights;
at least one vent;
a first controller;
a control panel;
 at least one first wireless communication module;
 a magnetic levitation mechanism;
 the at least one first wireless communication module, the at least one frequency-tone generator, the at least one oil-diffusing device, the at least one frequency-infusing device, and the first controller being mounted within the enclosure;
 the control panel, the first plurality of ambience lights and the at least one vent being integrated into the enclosure;
 the at least one frequency-infusing device being in fluid communication with the at least one oil-diffusing device;
 the at least one oil-diffusing device being in fluid communication with the at least one vent;
 the control panel, the at least one first wireless communication module, the at least one frequency-tone generator, the at least one oil-diffusing device, the at least one frequency-infusing device and the first plurality of ambience lights being electronically connected to the first controller;
 the enclosure comprises a top separable portion and a bottom separable portion;
 the top separable portion being attached onto the bottom separable portion;
 the at least one oil-diffusing device comprises at least one reservoir, an ultrasonic vibrator, at least one exhaust and a muffler;
 the at least one reservoir being removably situated within the bottom separable portion;
 the ultrasonic vibrator being mounted to a base of the at least one reservoir;
 the at least one reservoir and the ultrasonic vibrator being enclosed by the muffler;
 the at least one exhaust being in fluid communication with the at least one reservoir;
 wherein the at least one frequency-infusing device comprises a vibrating rod mounted through an opening of the at least one reservoir;
 wherein the magnetic levitation mechanism comprises a current-inducing module mounted within the bottom separable portion and electronically connected to the first controller and a magnet mounted within the top separable portion; and
 the magnet and the current-inducing module being magnetically coupled to each other.

2. The therapeutic device of claim 1, wherein:
the at least one oil-diffusing device further comprises a blower;
and
the blower being operatively integrated into the at least one exhaust, wherein the blower is used to draw fluid out of the at least one reservoir and to push fluid out of the at least one exhaust.

3. The therapeutic device of claim 1 further comprises:
a plurality of reflectors;
the top separable portion and the bottom separable portion being made of a translucent material;
the first plurality of ambience lights being integrated into the bottom separable portion;
the plurality of reflectors being integrated into the top separable portion; and
the first plurality of ambience lights being in optical communication with the plurality of reflectors.

4. The therapeutic device of claim 3, wherein:
the at least one vent being positioned adjacent to an apex of a pentagonal pyramid.

5. The therapeutic device of claim 3 further comprises:
a plurality of optical strips;
each of the plurality of optical strips comprises an arbitrary first light from the first plurality of ambience lights and an arbitrary reflector from the plurality of reflectors;
each of the plurality of optical strips being positioned along a corresponding lateral edge of a pentagonal pyramid; and
the arbitrary reflector being positioned in between the arbitrary first light and an apex of the pentagonal pyramid.

6. The therapeutic device of claim 3 further comprises:
a second plurality of ambience lights;
a plurality of optical strips;
each of the plurality of optical strips comprises an arbitrary first light from the first plurality of ambience lights and an arbitrary second light from the second plurality of ambience lights;
each of the plurality of optical strips being positioned along a corresponding lateral edge of a pentagonal pyramid; and
the arbitrary second light being positioned in between the arbitrary first light and an apex of the pentagonal pyramid.

7. The therapeutic device of claim 3 further comprises:
a plurality of leg stubs;
the plurality of leg stubs being externally mounted to a base of a pentagonal pyramid; and
the plurality of leg stubs being distributed across the base of the pentagonal pyramid.

8. The therapeutic device of claim 3, wherein:
a division plane between the top separable portion and the bottom separable portion being positioned in between an apex of a pentagonal pyramid and a base of the pentagonal pyramid; and
the division plane between the top separable portion and the bottom separable portion being positioned parallel to the base of the pentagonal pyramid.

9. The therapeutic device of claim 1 further comprises:
a second controller;
a second plurality of ambience lights;
at least one second wireless communication module;
the second plurality of ambience lights being integrated into the top separable portion;
the second controller and the at least one second wireless communication module being mounted within the top separable portion;
the second plurality of ambience lights and the at least one second wireless communication module being electronically connected to the second controller; and
the second controller being communicably coupled to the first controller.

10. The therapeutic device of claim 1, wherein:
the enclosure being shaped as a pentagonal pyramid.

* * * * *